(12) United States Patent  
Emami et al.

(10) Patent No.: US 12,037,468 B2
(45) Date of Patent: Jul. 16, 2024

(54) ULTRA-HIGH STRETCHABLE HYDROGEL, METHODS OF MAKING AND USE

(71) Applicant: Marquette University, Milwaukee, WI (US)

(72) Inventors: Shahriar Hojjati Emami, Milwaukee, WI (US); Lobat Tayebi, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 610 days.

(21) Appl. No.: 17/048,452

(22) PCT Filed: Apr. 17, 2019

(86) PCT No.: PCT/US2019/027823
§ 371 (c)(1),
(2) Date: Oct. 16, 2020

(87) PCT Pub. No.: WO2019/204404
PCT Pub. Date: Oct. 24, 2019

(65) Prior Publication Data
US 2021/0079171 A1 Mar. 18, 2021

Related U.S. Application Data

(60) Provisional application No. 62/660,355, filed on Apr. 20, 2018.

(51) Int. Cl.
*C08J 3/075* (2006.01)
*A61B 5/318* (2021.01)
(Continued)

(52) U.S. Cl.
CPC ............... *C08J 3/075* (2013.01); *A61B 5/318* (2021.01); *A61L 15/225* (2013.01);
(Continued)

(58) Field of Classification Search
None
See application file for complete search history.

(56) References Cited

U.S. PATENT DOCUMENTS 9,387,276 B2   7/2016  Sun et al.
2003/0232895 A1*  12/2003  Omidian ............... A61K 9/0065
521/134
(Continued)

FOREIGN PATENT DOCUMENTS

CA      02361971 A1 *  7/2001
JP      2004292592 A  * 10/2004
(Continued)

OTHER PUBLICATIONS

Algi et al., Highly Stretchable Self-Healing poly(N,N-dimethylacrylamide) Hydrogels, European Polymer Journal, 2014, 59:113-121.

(Continued)

*Primary Examiner* — Tae H Yoon
(74) *Attorney, Agent, or Firm* — Quarles & Brady LLP

(57) ABSTRACT

The present invention provides a stretchable hydrogel able to stretch over 200 times its length, methods of preparing such a hydrogel and compositions comprising the hydrogel.

19 Claims, 6 Drawing Sheets

(a)

(b)

(c)

(d)

(e)

(51) Int. Cl.
*A61L 15/22* (2006.01)
*A61L 26/00* (2006.01)
(52) U.S. Cl.
CPC ......... *A61L 26/008* (2013.01); *C08J 2323/06* (2013.01); *C08J 2333/26* (2013.01)

(56) References Cited

U.S. PATENT DOCUMENTS

| | | | |
|---|---|---|---|
| 2004/0001892 | A1 | 1/2004 | Healy et al. |
| 2009/0220578 | A1 | 9/2009 | King |
| 2012/0209396 | A1 | 8/2012 | Myung et al. |
| 2015/0038613 | A1 | 2/2015 | Sun et al. |
| 2017/0136180 | A1 | 5/2017 | Zhao et al. |

FOREIGN PATENT DOCUMENTS

| | | | |
|---|---|---|---|
| JP | | 4170187 B2 | 10/2008 |
| WO | WO 2009/134414 A2 | * | 11/2009 |
| WO | | 2017027590 A1 | 2/2017 |

OTHER PUBLICATIONS

Appel et al., Supramolecular Polymeric Hydrogels, Chemical Society Reviews, 2012, 41(18):6195-6214.
Bauer et al., Hydrogel Substrate Stress-Relaxation Regulates the Spreading and Proliferation of Mouse Myoblasts, Acta Biomaterialia, 2017, 62:82-90.
Chaudhary et al., Carboxymethylagarose-Based Multifunctional Hydrogel with Super Stretchable, Self-Healable Having Film and Fiber Forming Properties, Arabian Journal of Chemistry, 2020, 13(1):1661-1668.
Chaudhuri et al., Hydrogels with Tunable Stress Relaxation Regulate Stem Cell Fate and Activity, Nature Materials, 2016, 15(3):326-334.
Fitzgerald et al., Tunable Stress Relaxation Behavior of an Alginate-Polyacrylamide Hydrogel: Comparison with Muscle Tissue, Biomacromolecules, 2015, 16(5):1497-1505.
Huang et al., Energy-Dissipative Matrices Enable Synergistic Toughening in Fiber Reinforced Soft Composites, Advanced Functional Materials, 2017, 27(9):1605350, 10 pages.
Jeon et al., Single and Dual Crosslinked Oxidized Methacrylated Alginate/PEG Hydrogels for Bioadhesive Applications, Acta Biomaterialia, 2014, 10(1):47-55.
Jeon et al., Extremely Stretchable and Fast Self-Healing Hydrogels, Advanced Materials, 2016, 28:4678-4683.
Kakuta et al., Preorganized Hydrogel: Self-Healing Properties of Supramolecular Hydrogels Formed by Polymerization of Host-Guest-Monomers that Contain Cyclodextrins and Hydrophobic Guest Groups, Advanced Materials, 2013, 25(20):2849-2853.
Kim et al., Hydrogel-Laden Paper Scaffold System for Origami-Based Tissue Engineering, Proceedings of the National Academy of Sciences, 2015, 112(50):15426-15431.
Kocen et al., Viscoelastic Behaviour of Hydrogel-Based Composites for Tissue Engineering under Mechanical Load, Biomedical Materials, 2017, 12(2):025004, pp. 1-11.
Kramb et al., Belousov-Zhabotinsky Hydrogels: Relationship between Hydrogel Structure and Mechanical Response, Chemistry of Materials, 2015, 27(16):5782-5790.
Kumar et al., Flexible and Microporous Chitosan Hydrogel/Nano ZnO Composite Bandages for Wound Dressing: In Vitro and In Vivo Evaluation, ACS Applied Materials & Interfaces, 2012, 4(5):2618-2629.
Lee et al., Preparation of Interpenetrating Polymer Network Composed of poly(ethylene glycol) and poly(acrylamide) Hydrogels as a Support of Enzyme Immobilization, Polymers for Advanced Technologies, 2008, 18:852-858.
Lee et al., A Mechanical Metamaterial Made from a DNA Hydrogel, Nature Nanotechnology, 2012, 7(12):816-820.
Li et al., Designing Hydrogels for Controlled Drug Delivery, Nature Reviews Materials, 2016, 1(12):1-17.
Lin et al., Stretchable Hydrogel Electronics and Devices, Advanced Materials, 2016, 28(22):4497-4505.
Liu et al., Injectable Hydrogels for Cartilage and Bone Tissue Engineering, Bone Research, 2017, 5(1):17014, pp. 1-20.
Meyvis et al., A Comparison Between the Use of Dynamic Mechanical Analysis and Oscillatory Shear Rheometry for the Characterisation of Hydrogels, International Journal of Pharmaceutics, 2002, 244(1-2):163-168.
Schmoller et al., Similar Nonlinear Mechanical Responses in Hard and Soft Materials, Nature Materials, 2013, 12(4):278-281.
Srikumar et al., Biofabrication of Interpenetrating Polymer Network Hydrogels, Ergonomics International Journal, 2017, 1(3):000114, 6 pages.
Sun et al., Highly Stretchable and Tough Hydrogels, Nature, 2012, 489(7414):133-136.
Wang et al., Synthesis of Efficient and Reusable Catalyst of Size-Controlled Au Nanoparticles within a Porous, Chelating and Intelligent Hydrogel for Aerobic Alcohol Oxidation, Journal of Molecular Catalysis A: Chemical, 2010, 317(1-2):81-88.
Wang et al., B12-Dependent Photoresponsive Protein Hydrogels for Controlled Stem Cell/Protein Release, Proceedings of the National Academy of Sciences, 2017, 114(23):5912-5917.
Weng et al., Rheological Characterization of In Situ Crosslinkable Hydrogels Formulated from Oxidized Dextran and N-carboxyethyl Chitosan, Biomacromolecules, 2007, 8(4):1109-1115.
Wu et al., A Robust, Highly Stretchable Supramolecular Polymer Conductive Hydrogel with Self-Healability and Thermo-Processability, Scientific Reports, 2017, 7:41566, 11 pages.
Xu et al., Environmentally Friendly Hydrogel-Based Triboelectric Nanogenerators for Versatile Energy Harvesting and Self-Powered Sensors, Advanced Energy Materials, 2017, 7(1):1601529, pp. 1-8.
Yan et al., Rheological Properties of Peptide-Based Hydrogels for Biomedical and Other Applications, Chemical Society Reviews, 2010, 39(9):3528-3540.
Yue et al., Mechano-Actuated Ultrafast Full-Colour Switching in Layered Photonic Hydrogels, Nature Communications, 2014, 5(1):1-8.
Zhu et al., A High Modulus Hydrogel Obtained from Hydrogen Bond Reconstruction and Its Application in Vibration Damper, RSC Advances, 2017, 7(69):43755-43763.
PCT International Search Report and Written Opinion, PCT/US2019/027823, dated Jul. 10, 2019, 15 pages.

* cited by examiner (a)

(b)

(c)

(d)

(e)

ULTRA-HIGH STRETCHABLE HYDROGEL, METHODS OF MAKING AND USE

CROSS-REFERENCE TO RELATED APPLICATIONS

This application represents the U.S. national stage entry of International Application No. PCT/US2019/027823 filed Apr. 17, 2019, which claims the benefit of U.S. Provisional Patent Application No. 62/660,355 filed Apr. 20, 2018, which disclosures are incorporated herein by reference in their entirety.

STATEMENT REGARDING FEDERALLY SPONSORED RESEARCH

N/A

BACKGROUND OF THE INVENTION

The field of the invention is related to ultra-stretchable hydrogels.

Interest in hydrogels is growing at a fast pace, and much scientific literature publications and industrial aptness has been reported in the last decade or so. TO a large extent, this consensus attractiveness is due to the biomedical applications of the hydrogels for scaffolds in tissue engineering, control release drug delivery, wound dressing and bioadhesives.[1-6] The new emerging applications for these materials even added more value to an already advantageous properties, including stretchable electronics, intelligent, smart and meta materials as well as supramolecular ones are very eye catching and vivid fields.[7-11] In foreseeable future we may even expect and hear more about computing, conducting, aerospace and energy harvesting hydrogels.[12-15]

There is a need for new and improved hydrogels with improved properties, including improved stretchability over the prior materials.

SUMMARY OF THE INVENTION

The present invention overcomes the aforementioned drawbacks by providing an ultra-high stretchable material which provides a stretchability of 260 times increase in original length (26000% increase). This ultra-high stretchable material can be used in stretchable embedded electronics or contour forming wound coverings, and other materials in which highly stretchable material is desired.

In one aspect, the disclosure provides a stretchable hydrogel comprising N,N'-dimethylacrylamide (DMA) and polyethylene oxide (PEO) forming a semi-interpenetrating polymer network (IPN), wherein the stretchable hydrogel is able to increase its length at least about 30-200 times its original length when stretched.

In another aspect, the present disclosure provides a method of making a stretchable hydrogel able to increase its length by at least 30-200 times its initial length, the method comprising the step of: (a) polymerizing N,N'-dimethylacrylamide (DMA) in the presence of polyethylene oxide (PEO), thus forming a semi-interpenetrating polymer network (IPN) to form a stretchable hydrogel.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

DETAILED DESCRIPTION OF THE INVENTION

Figure 1A:
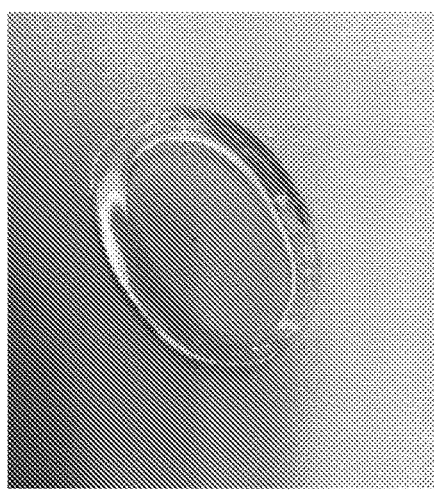
FIGS. 1A-1E. Hydrogel before and after being stretched and possible design of use. Hydrogel prior to experiments (a), hydrogel prior to stretching (b), stretched hydrogel prior to fully drawn one (c) stretched hydrogel prior to breaking point (d) Iclone software design shows possible application as wound dressing for hands (e).
Figure 1B:
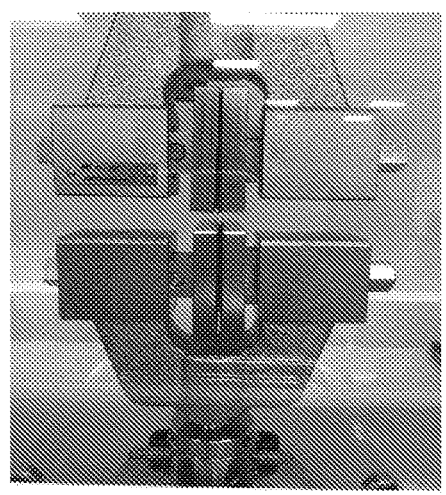
Figure 1C:
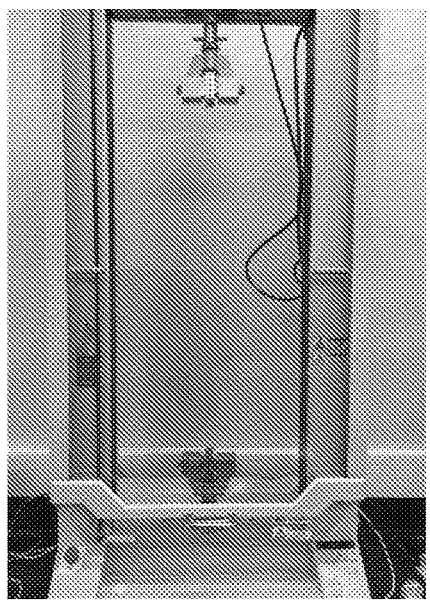
Figure 1D:
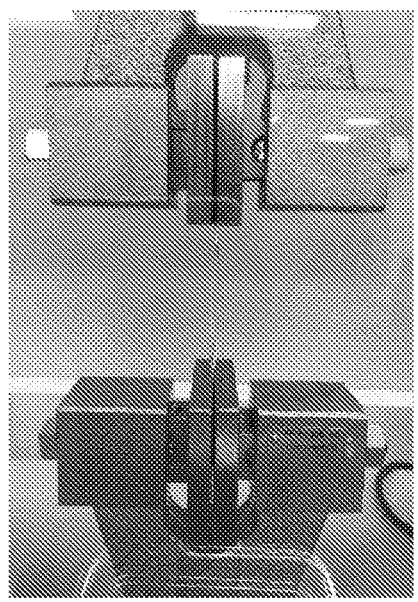
Figure 1E:

A quest for finding highly stretchable materials is an ongoing challenge in many laboratories around the world. Hydrogels are typically elastic and good candidates for very large length increase. Here we provide a hydrogel that demonstrates 30-260 times increase in original length or 3000-26000%.

Stretchable Hydrogel and Compositions

The present invention provides a stretchable hydrogel comprising, consisting essentially of, or consisting of, N,N'-dimethylacrylamide (DMA) and polyethylene oxide (PEO) forming a semi-interpenetrating polymer network (IPN) wherein the stretchable hydrogel is able to increase its length, in one embodiment, at least 30-200 times (e.g., 3000-20000%) when stretched. In a preferable embodiment, the stretchable hydrogel is able to increase its length at least 100-250 times (e.g., 10000-25000%) when stretched (e.g., about 260 times, or 26000%). In some embodiments of the invention, the preferred stretchability is unexpectedly 10-fold higher than the prior art (which shows 20 time stretchability, See Sun, J.-Y., et al. Highly stretchable and tough hydrogels. Nature 489, 133-136 (2012)) providing superior stretchability for the myriad of applications the hydrogel may be used.

In some embodiments, the stretchable hydrogel is able to increase its length at least about 30-250 times, alternatively about 50-250 times, alternatively about 100-250 times, alternatively about 150-250 times, alternatively about 200-

250 times its original length, alternatively about 30-200 times, alternatively 30-100 times, and include any range or amount of stretchability in-between (e.g., 30 times, 35 times, 40 times, 45 times, 50 times, 75 times, 85 times, 95 times, 100 times, 125 times, 150 times, 175 times, 200 times, 225 times, 250 times, 260 times, etc.)

In one embodiment, the stretchable hydrogel consists of N,N'-dimethylacrylamide (DMA) and polyethylene oxide (PEO). In one embodiment, the N,N'-dimethylacrylamide (DMA) is polymerized in the presence of polyethylene oxide (PEO) to make the stretchable hydrogel. In a preferred embodiment, the DMA and PEO form a semi-IPN, as defined below.

The hydrogel of the present invention is made of two non-ionic polymers forming a semi-IPN. The present invention does not use any hydrophobic or ionic material in the hydrogel formula. The hydrogel of the present invention uses two non-ionic based polymers prepared from polymerized N,N-Dimethylacrylamide monomer and Polyethylene oxide polymer.

The hydrogel of the present invention has a profound ability to encompass almost 100% increase in stress relaxation after more than 20 hours from 0.1 N to 0.2 N. The hydrogels also display a sharp contrast with typical decrease in time sweep stress relaxation curves of prior hydrogels. As demonstrated in the examples, energy damping for more than 10 times between first and second cyclic loading highlights polymer chain interactions as a key characteristic for extending materials well beyond their expected lengths and the currently highly stretchable hydrogel. Not to be bound by any theory, but it is thought that the lightly crosslinked PDMA keeps the hydrogel structure intact but polyether structure of PEO (with potential to produce numerous hydrogen bonds) promotes dynamic non-covalent bonds with PDMA. This structure of the hydrogel is able to undergo energy dissipation mechanism through breakage of bonds upon strain exertion. A material with strain accommodating architecture can intrinsically stretch and repair itself after large mechanical deformation. In one embodiment, the amount of deformation is fixed for two cycles at 100 mm.

As used herein, non-ionic polymers are polymers that do not contain ionic bonds in their molecular structure. As used herein, "hydrophobic polymer" is a pre-formed polymer network having at least one of the following two properties: (1) a surface water contact angle of at least 45° and (2) exhibiting water absorption of 2.5% or less after 24 hours at room temperature according to ASTM test standard D570.

As used herein, "ionic material" or "ionic polymers" are materials or polymers, either organic or inorganic, which contain both covalent and ionic bonds in their molecular structure. For use herein, an ionic polymer is defined as a polymer comprised of macromolecules containing at least 2% by weight ionic or ionizable monomers (or both), irrespective of their nature and location. An "ionizable monomer" is a small molecule that can be chemically bonded to other monomers to form a polymer and which also has the ability to become negatively charged due the presence of acid functional groups such carboxylic acid and/or sulfonic acid.

For purposes of this application, an interpenetrating polymer network (IPN) is a polymer comprising two or more polymers networks where at least one of the polymers is polymerized and/or cross-linked in the immediate presence of the other such that the networks of polymers are at least partially interlaced on a polymer scale but not covalently bonded to each other. The IPN formed network cannot be separated unless chemical bonds are broken. A semi-interpenetrating polymer network (semi-IPN) is a polymer comprising one or more polymer networks and one or more linear or branched polymers characterized by the penetration on a molecular scale of at least one of the networks by at least some of the linear or branched macromolecules. Semi-IPN is distinguished from an IPN because the semi-IPN is a polymer blend where the constituent linear or branched macromolecules can, in principle, be separated from the constituent polymer network(s) without breaking chemical bonds.

In one embodiment, the stretchable hydrogel has about 100% increase in stress relaxation after more than 20 hours from 0.1 N to 0.2 N. In one embodiment, the hydrogel is able to return to pre-stretched size after being stretched at least 200 times its length.

In another embodiment, the present invention provides compositions comprising the stretchable hydrogel described herein. Suitable compositions may be used for a myriad of applications in which a highly stretchable hydrogel are required.

For example, the hydrogel may be used in compositions for wound care and in wound dressings, for example, a contour forming wound covering. The dressings using the hydrogel and obtained can be used for dressing any kind of wounds. The composition provides flexibility, the ability to prevent bacteria from penetrating the wounds or other infections from external microbial pathogens, and prevents water loss from the wound. The hydrogel wound dressing formed may have an excellent tensile strength, so it is not easily torn when it is applied to a wound. Further, in some embodiments, the hydrogel will not bind or stick to a wound and cause secondary wound damage when it is changed. Suitably, the hydrogel composition has no cytotoxicity, acute toxicity, irritability, and it will not irritate the skin.

Suitable wounds to be treated include, scrapes, cuts, burns, and larger area skin wounds, especially wounds that occur around joints or other areas in which the skin flexes and the wound dressing would need greater stretchability.

In some embodiments, the composition comprises the stretchable hydrogel and one or more components, such as, for example, drug delivery components, electronic devices, electronic sensors, deformable conductors, or rigid electronic components incorporated therein. The composition provides an interface formed between the hydrogel and the various components to provide a hydrogel composition in which the reliability and functionality of the incorporated components are maintained even under large deformation pressures (e.g., stretched) and from which one or more functions can be performed regardless of the state of the deformation (stretching).

In some embodiments, the embedded component is an electronic sensor, for example, a sensor that monitors one or more conditions within a subject, for example, a heart rate monitor, an electrocardiogram (EKG or ECG) electrode, temperature sensor, stretchable dresses, or the like.

In some embodiments, the component is an electrode to provide reliable low impedance electrical contact with the skin for physiological measurements (e.g. heart rate monitoring, cardiac monitoring, etc.).

The term "maintaining their functionality and reliability", generally means that the overall operation of the component within the hydrogel composition remains the same or substantially the same regardless of the state of deformation. In particular, deformation or stretching of the hydrogel composition does not cause the components to become disengaged or disconnected from the hydrogel. Further, deformation of the hydrogel composition does not cause the components (i.e., the drug delivery components, the electronic components, and electronic sensors) to cease operation or to operate differently or substantially differently than the components operate when the hydrogel composition is not subjected to deformation (e.g., stretched). A substantial difference in functionality or reliability of the components would be a difference that results in the embedded component not functioning as needed or as intended (e.g., failure of one or more sensors to properly monitor one or more conditions, failure of the sensors to transmit measured conditions, etc.).

In one embodiment, the embedded electronic device is a heart rate monitor, an EKG electrode, a temperature sensor, or the like.

In one embodiment, the composition of the present can be used to monitor cardiac events, for example, can be used in methods and compositions to provide an electrocardiogram. Suitably, in some embodiments, the present disclosure provides a composition comprising the stretchable hydrogel described herein and one or more EKG electrodes embedded within one or more hydrogels of the present invention. In some embodiments, methods of producing an EKG using the composition described herein are provided.

In another embodiment, the hydrogel and compositions described herein can be used in a drug delivery system. For example, the hydrogel may be used as a patch for transdermal controlled release of a drug formulation. Suitable transdermal drugs are known in the art. In one embodiment, the invention includes a drug delivery system comprising the hydrogel described herein and a drug encapsulated or embedded within the hydrogel, wherein the hydrogel allows for a desired release rate of the drug from the hydrogel. In some embodiments, the hydrogel may be used in the composition for an implantable drug delivery system. The drug may be an active ingredient or formulation to treat one or more diseases. Suitable active agents may be, for example, a drug, a nutraceutical, and/or a pharmaceutical agent.

In another embodiment, the hydrogels may be used for wound treatment. In some embodiments, the hydrogels may be formulated into a composition comprising one or more wound treatments, for example, anti-bacterial or anti-fungal treatments. In one embodiment, the present disclosure provides compositions for wound dressing comprising the hydrogel described herein and one or more anti-microbial agent, for example, one or more antibacterial, antiseptics, antifungal, or antiviral agents. Suitable anti-microbial agents are known in the art. For example, suitable anti-bacterial agents include, but are not limited to, topical antibiotics (e.g., but not limited to, bacitracin, cortisporin, polymyxin B, neomycin, mupirocin, erythromycin, retapamulin, gentamicin, ozenoxacin, silver sulfadiazine, mafenide, metronidazole, among others. These examples are for illustrative purposes only and are not meant to be limiting to the compositions described herein.

Methods of Making Stretchable Hydrogel

The present invention also provides methods of making the stretchable hydrogel described herein that is able increase its length by at least 200 times, the method comprising the step of (a) polymerizing N,N'-dimethylacrylamide (DMA) in the presence of polyethylene oxide (PEO), thus forming a semi-interpenetrating polymer network (IPN) to form a stretchable hydrogel.

In some embodiments, step (a) was performed at 50° C. with ammonium persulfate as an initiator and N,N-methylenebisacrylamide as crosslinking agent to polymerize the DMA and PEO for at least one hour.

In further embodiments, the method comprises after polymerization, submersing the hydrogel in water for at least 1 hour.

Further, the method comprises purging the reaction mixture with inert gas for at least 10 minutes.

The above description, attached figures, and claims listed below are intended to be illustrative and not limiting of this invention. In light of the invention described herein, many themes and variations to this invention will be suggested to one skilled in the art. All such themes and variations are within the contemplation hereof. For instance, while this invention has been described in conjunction with the various exemplary embodiments outlined above and in the below claims, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/ or substantial equivalents of these exemplary embodiments.

It is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1: Preparation of an Ultra-High Stretchable Hydrogel

This Example demonstrates a hydrogel with ultra-high ability to stretch. This ultra-high stretchable material will have relevance in stretchable embedded electronics or contour forming wounds. The enormous ability for length increase may be attributed to low characteristic ratio of polyethylene oxide (PEO) and random coil opening of entangled polymer chains.

Hydrogels are made up of two coexisting components, liquid doesn't let the solid to collapse and solid won't permit the liquid to flow. We have synthesized a material with the ability to stretch to a large extent by incorporating polyethylene oxide chains in network of poly dimethyl acrylamide. N,N'-dimethylacrylamide (DMA) polymerized in presence of polyethylene oxide and forms a semi-interpenetrating polymer network (IPN) or semi-IPN. Polyether chains of PEO with oxygen in backbone impose high flexibility to entangled chains for contouring, shape forming, and rod formation upon stress exertion. Distribution of PEO chains inside the PDMS network structure divert exerted stress from crosslink junctions to long spaghetti shape PEO chains anchored to the structure. Upon stress enclosure, force transfers to the PEO random coil chains, with low characteristic ratio, and start to open them up without much slippage. While the network structure is being stretched, the PEO chains straighten up and presumably since they hooked to the network junctions their only choice is extension. Two methyl groups are good anchoring points for flexible linear PEO chains to anchor and make physical knots. Stretching sample will open up almost all of the highly coiled PEO chains until rod shape chains start to form.

Figure 2A:
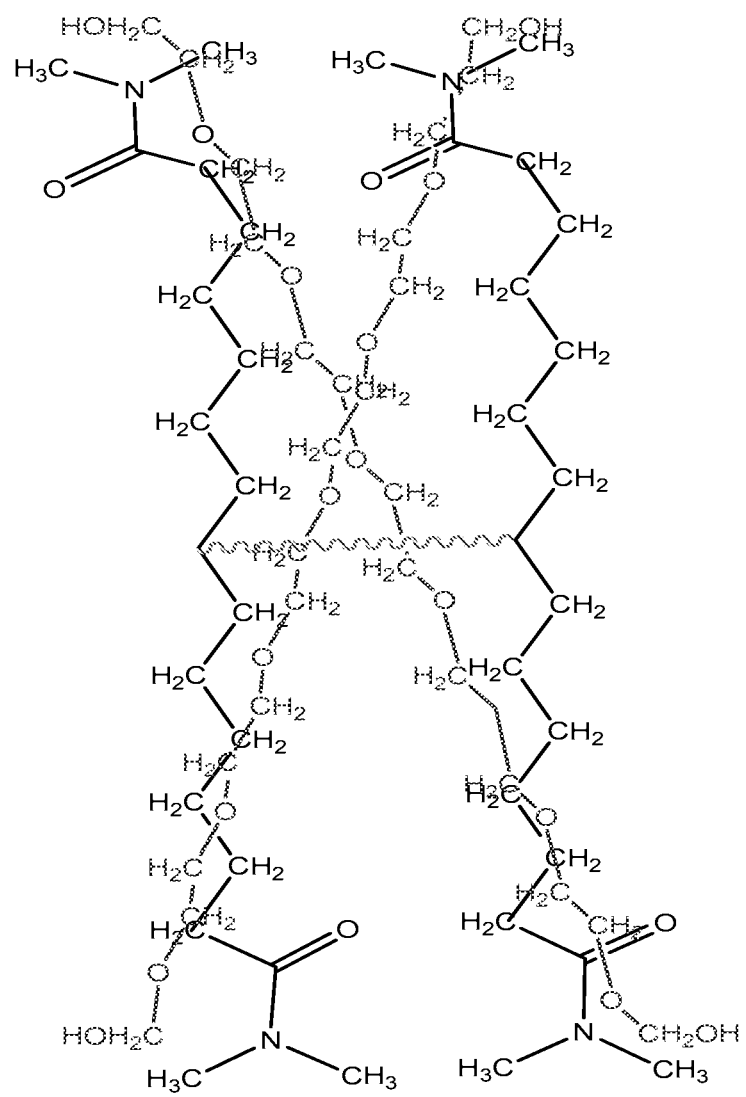
FIG. 2A is a schematic illustration of possible structures and gelation of lightly crosslinked PDMS chains with one crosslinking junction, uncoiled PEO chains hangs through the network and may slide until dock with methyl groups (a).
Figure 2B:
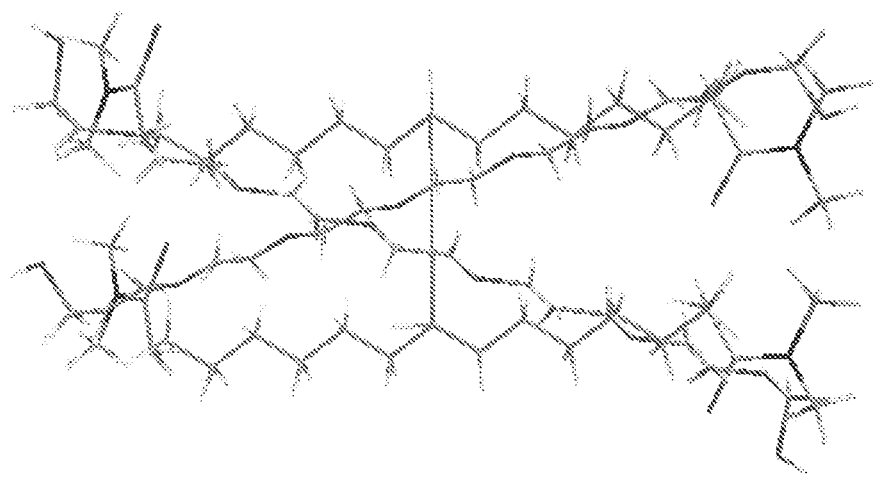
FIG. 2B is a 3D stick design of above proposed structure described in FIG. 2A.
Figure 2C:
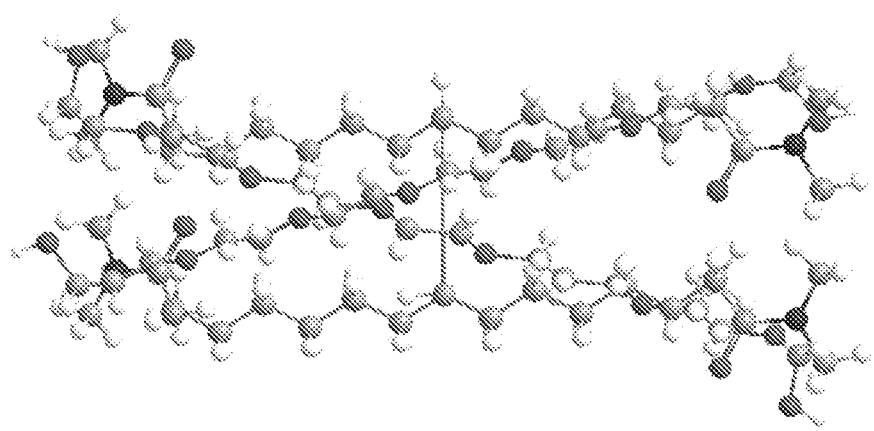
FIG. 2C is a 3D ball and stick design of the proposed structure.

FIG. 1 depicts hydrogel sample after synthesis, in tensile machine grips and after stretching. FIG. 2 shows a hypothetical design of possible semi-IPN structure in tension and its three dimensional design. The plausible phenomena happening in this system is diverting tensile strain from breaking junction points to stretch PEO chains. In other words, energy is dissipating by linear chains.

Figure 3:
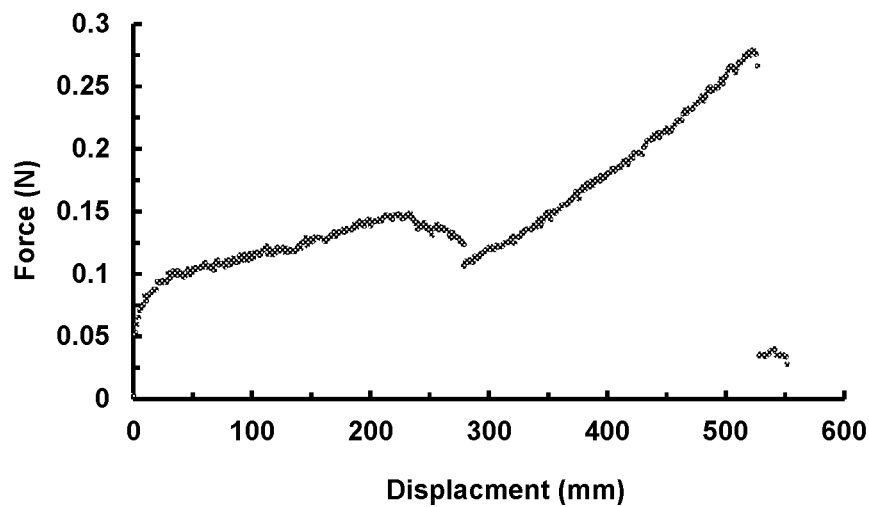
FIG. 3 is a graph depicting the ultimate tensile strength experiment of PDMS-PEO IPN hydrogel with a pause at around 270 mm displacement for grip tightening.

The high stretchability of the sample is seen in FIG. 3. In this experiment, the test was paused to increase tightness to upper and lower clamps since sample grip slippage was dominant and hindering sample breakage. Inserting excess force to the grips at the starting point causes sample vulnerable to shear force premature cut off. FIG. 3 illustrates more than 260 times or 26000% increase in length, an enormous elongation compared to original 2 mm gauge length. The graph indicates the slow pace increase in tensile strength until around midpoint where an abrupt increase in strength is obvious that points out to dominating PEO chains straightening up. Moreover, the first half of the graph is very similar to rubber tensile test prior to random coil unzipping domination. Although the breaking point, to the best of our knowledge, surpasses the previous reports, the sample breaking close to the grips indicates that shear stress at grips can cause premature break and probably extension thinning would go further if the grip point shear weakening could have been overcome. Since the diameter of original sample was 3.1 mm and force at break is around 0.27 N, therefore, strength at breaking point is close to 9 KPa.

Figure 4:
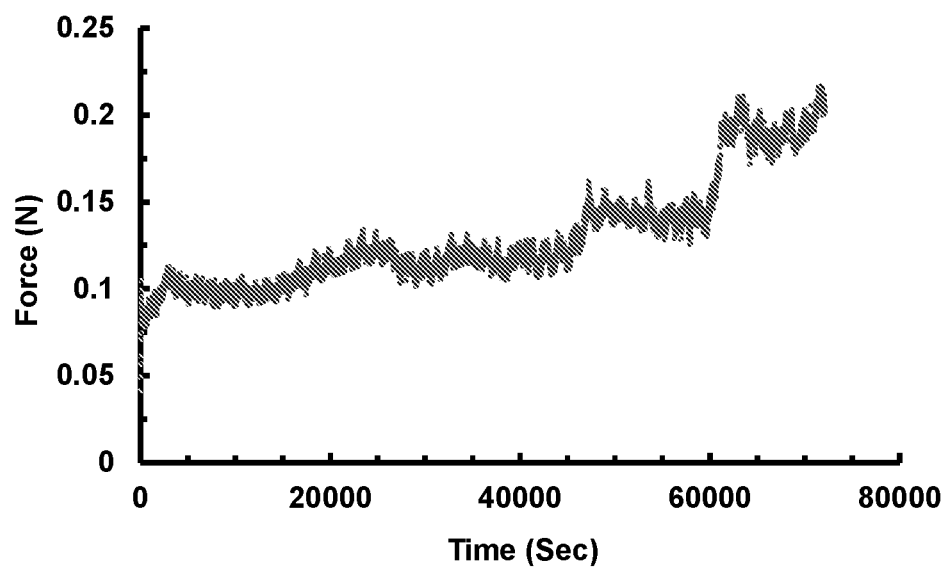
FIG. 4 is a graph depicting relaxation experiment overnight for 20 hours at 150 mm extension with gradual and more than 100% increase in force bearing.

The relaxation test was performed at 150 mm displacement for 20 hours and, as seen in FIG. 4, force is gradually and steadily increasing to 0.2 N and is not similar to typical stress relaxation curves. All materials usually show decrease in stress bearing by increasing time and this material depicts an opposite behavior.[18-20] Not to be bound by any theory, the reason may be due to the incremental random coils opening in twenty hours inferring stronger force bearing in time sweep experiment. This behavior is especially appealing for the applications that needs a material to stay intact under constant stress. Although for the first hour or so the increase in relaxation time may relate to drying process of gel, even in complete drying state after around 16-17 hours a steep step increase in stress is obvious. It highlights an increase in stress at constant strain.

Figure 5:
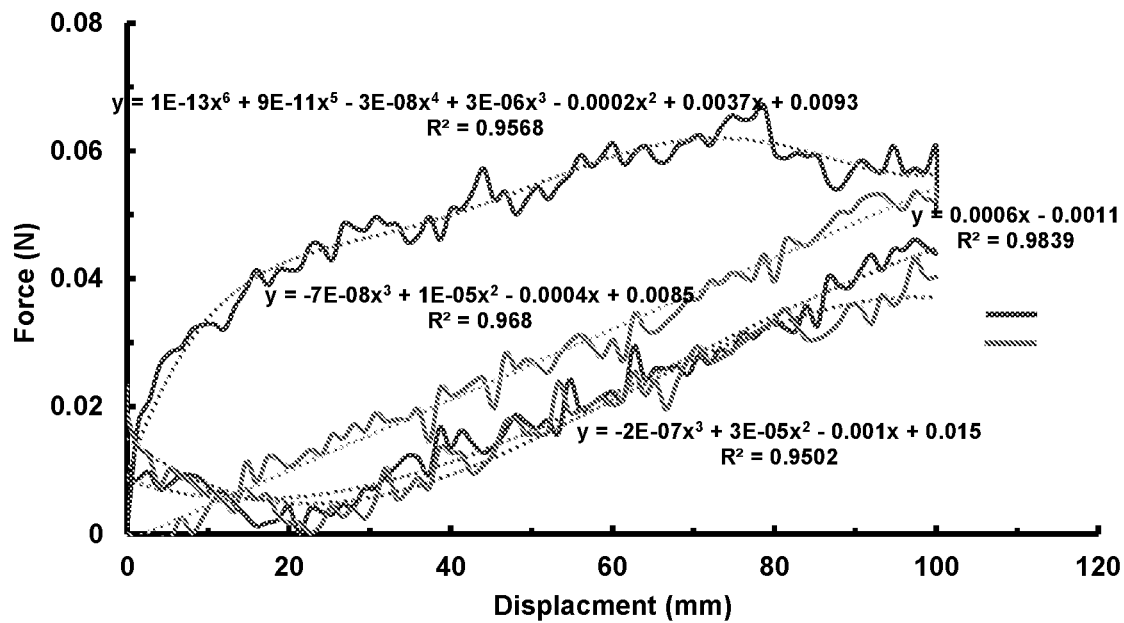
FIG. 5 is a graph depicting cyclic tensile-compression experiment, dotted trend line and fitting equations are used in Wolframalpha integration to calculate area under each cycle.
Figure 6:
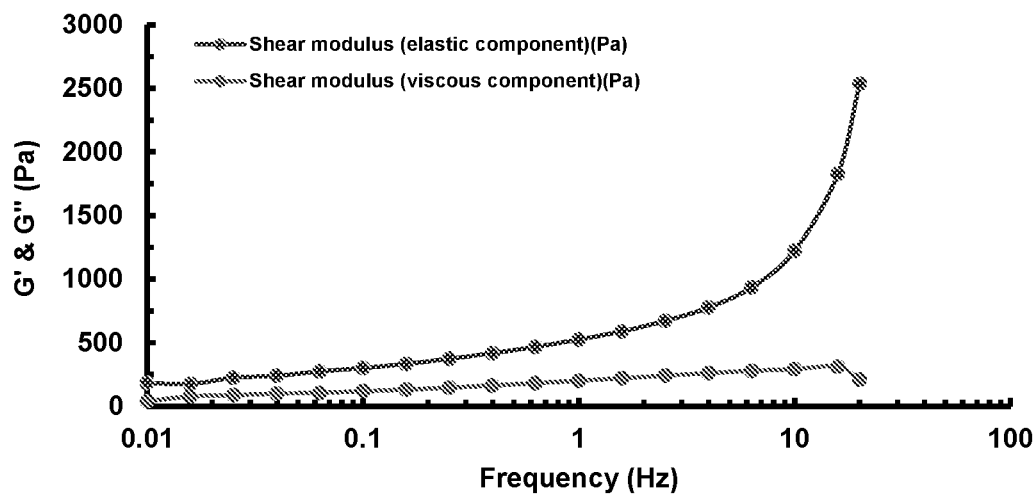
FIG. 6 is a graph depicting dynamic mechanical analysis performed in parallel plates Rheometer in shear mode and frequency sweep.

Hydrogels cyclic loading and hysteresis studies have been reported in previous literatures.[21,22] Cycling in two consecutive tensile and compression tests in FIG. 5 revealed that energy damping in first loop is more than 10 times larger than the second loop and most of the energy is being dissipated within polymer chains in first cycle of the loading-unloading, tensile-compression experiment. The polynomial equations obtained by trend line fitting to curves in Microsoft Excel software and area between curves for each cycle was calculated by integration using online service Wolframalpha computational knowledge engine. The large amount of energy dissipation in the first loop may confirm our observation that internal structure change, presumably due to loss of PEO chains reoccurring elasticity, hinders ultra-high stretch ability after first contraction. In other words, once the chains uncoil and retract elasticity is reduced to a large extend.

$$\int_0^{100} [(1 \times 10^{-13} X^6 + 9 \times 10^{-11} X^5 - 3 \times 10^{-8} X^4 +$$
$$3 \times 10^6 X^3 - 2 \times 10^{-4} X^2 + 3.7 \times 10^{-3} X + 9.3 \times 10^{-3}) -$$
$$(-7 \times 10^{-8} X^3 + 1 \times 10^{-5} X^2 - 4 \times 10^{-4} X + 8.5 \times 10^{-3})]$$
$$dX = -16.24$$

$$16.2414 \text{(absolute value)} N \cdot mm (1000 \, N \cdot mm = 1 \, J) =$$
$$1624 \times 10^{-2} \, J/[7.54 \, mm^2 \text{(cross sectional area before experiment)} *$$
$$2 \, mm \text{(gap length)}] = 1 \times 10^{-3} \, J/mm^3$$

$$\int_0^{100} [(6 \times 10^{-4} X - 1.1 \times 10^{-3}) - (-2 \times 10^{-7} X^3 + 3 \times 10^{-5} X^2 -$$
$$1 \times 10^{-3} X + 1.5 \times 10^{-2})]dX = 1.39$$

$$1.39 \, N \cdot mm = 139 \times 10^{-3} \, J/15.08 \, mm^3 = 9.218 \times 10^{-5} \, J/mm^3$$

Figure 7:
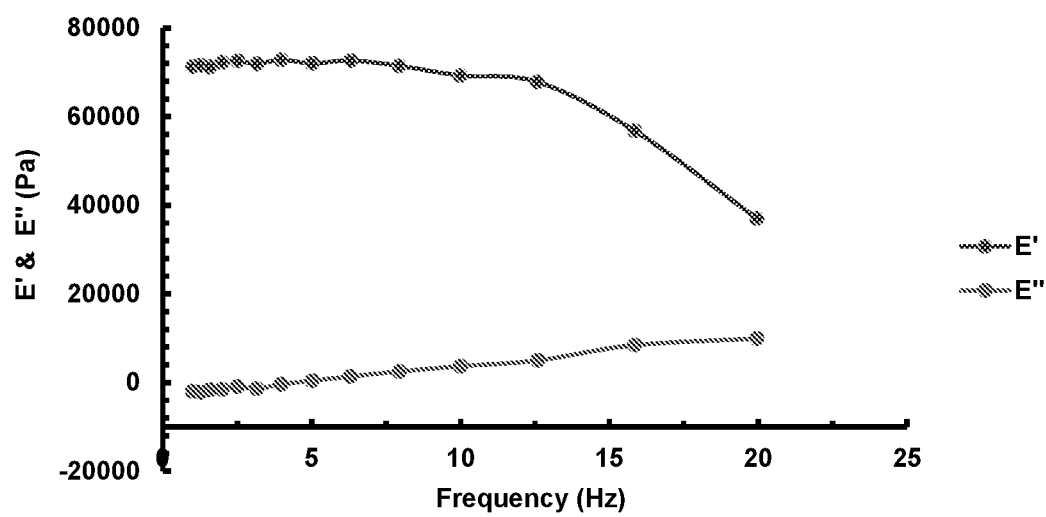
FIG. 7 is a graph depicting dynamic mechanical analysis performed in tensile fixture or axial geometry at frequency sweep mode.

Rheological properties of hydrogels have been studied in prior arts.[23,24] Dynamic mechanical analysis in shear mode revealed an increasing trend in storage modulus or G' at frequencies above 10 Hz and FIG. 5 depicts its strong elastic behavior up to 2500 pa at around 20 Hz. This result may confirm our previous experiments that significant damping is observed in the first cycle, pointing to viscose part, G", domination at static state with large amount of chains anchoring to PDMS network. Dynamic mechanical analysis in axial mode for hydrogels has been reviewed in few prior articles and FIG. 7 reveals a contrast result compare to shear mode experiment, reducing E' by increasing frequency.[25-27] The discrepancy in FIG. 7 may well described by unique structure of entangled chains that resist movement in dynamic shear force. However, in axial direction, although entangled chains have the major role in static large extensibility but in dynamic mode since PEO chains are physically bonded, at above 12 Hz, start to loosen up drastically with steep reduction in axial storage modulus.

METHODS

Synthesis

N,N'-Dimethyl acrylamide (Aldrich 99%) inhibitor was removed and purged with Nitrogen gas for at least 10 minutes. Polymerization and crosslinking was performed in water bath at 50° C. with Ammonium persulfate (Sigma 98%) as an initiator and N,N'-Methylenebisacrylamide (Sigma 99%), as crosslinking agent; after Polyethylene oxide (2,000,000 Aldrich) addition to reaction vessel. After polymerization and crosslinking, water was added to the sample and stayed for at least one hour before removing sticky hydrogel from the reaction vessel by a spatula.

Mechanical Tensile Experiment

Tensile experiment (Shimadzu AGS-X 5KN) was exerted on the hydrogel to find out ultimate strength at break. Hydrogel was mounted between upper and lower jaws and adjusted to stick in upright position. Grips were tightening up, to avoid slippage at high extensions, but not to the extent to cut the sample from over exert shear force. Excess force to the grips caused shear stress to cut or weaken sample. The experiment was run at 2 mm gap length (at 5 mm gap length machine was reached to its highest limit) at 80 mm/s head speed and a number of collected points adjusted to 1 point per second. The experiment was paused at 272 mm extension as jaws were tighten up again prior to resuming tensile force. Stress relaxation was performed with same instrument as well.

Rheometer

A parallel plate 2 cm geometry with 1 mm gap setting (Malverin Instruments Inc., Kinexus) was used to test hydrogel sample in shear mode. Frequency sweep was performed from 0.01 Hz to 20 Hz to observe hydrogel storage and loss modulus behavior at different frequencies. The sample was stuck to the parallel plate and no effective slippage was observed during the frequency sweep.

Dynamic Mechanical Experiment in Axial Mode

The experiment was run with tensile geometry (Perkin Elmer DMA 8000) from 0.01 Hz to 20 Hz. Hydrogel was fixed between grips and covered with equipment fixture.

REFERENCES

1. Liu, M., et al. Injectable hydrogels for cartilage and bone tissue engineering. *Bone research* 5, 17014 (2017).
2. Kim, S.-H., et al. Hydrogel-laden paper scaffold system for origami-based tissue engineering. *Proceedings of the National Academy of Sciences* 112, 15426-15431 (2015).
3. Wang, R., Yang, Z., Luo, J., Hsing, I.-M. & Sun, F. B12-dependent photoresponsive protein hydrogels for controlled stem cell/protein release. *Proceedings of the National Academy of Sciences* 114, 5912-5917 (2017).
4. Li, J. & Mooney, D. J. Designing hydrogels for controlled drug delivery. *Nature Reviews Materials* 1, 16071 (2016).
5. Sudheesh Kumar, P., et al. Flexible and microporous chitosan hydrogel/nano ZnO composite bandages for wound dressing: in vitro and in vivo evaluation. *ACS applied materials & interfaces* 4, 2618-2629 (2012).
6. Jeon, O., Samorezov, J. E. & Alsberg, E. Single and dual crosslinked oxidized methacrylated alginate/PEG hydrogels for bioadhesive applications. *Acta biomaterialia* 10, 47-55 (2014).
7. Lin, S., et al. Stretchable hydrogel electronics and devices. *Advanced Materials* 28, 4497-4505 (2016).
8. Wang, Y., Yan, R., Zhang, J. & Zhang, W. Synthesis of efficient and reusable catalyst of size-controlled Au nanoparticles within a porous, chelating and intelligent hydrogel for aerobic alcohol oxidation. *Journal of Molecular Catalysis A: Chemical* 317, 81-88 (2010).
9. Kakuta, T., et al. Preorganized Hydrogel: Self-Healing Properties of Supramolecular Hydrogels Formed by Polymerization of Host-Guest-Monomers that Contain Cyclodextrins and Hydrophobic Guest Groups. *Advanced materials* 25, 2849-2853 (2013).
10. Lee, J. B., et al. A mechanical metamaterial made from a DNA hydrogel. *Nature nanotechnology* 7, 816-820 (2012).
11. Appel, E. A., del Barrio, J., Loh, X. J. & Scherman, O. A. Supramolecular polymeric hydrogels. *Chemical Society Reviews* 41, 6195-6214 (2012).
12. Kramb, R. C., Buskohl, P. R., Dalton, M. J. & Vaia, R. A. Belousov-Zhabotinsky hydrogels: Relationship between hydrogel structure and mechanical response. *Chemistry of Materials* 27, 5782-5790 (2015).
13. Wu, Q., et al. A robust, highly stretchable supramolecular polymer conductive hydrogel with self-healability and thermo-processability. *Scientific Reports* 7, 41566 (2017).
14. Huang, Y., et al. Energy-Dissipative Matrices Enable Synergistic Toughening in Fiber Reinforced Soft Composites. *Advanced Functional Materials* 27(2017).
15. Xu, W., et al. Environmentally Friendly Hydrogel-Based Triboelectric Nanogenerators for Versatile Energy Harvesting and Self-Powered Sensors. *Advanced Energy Materials* 7(2017).
16. Sun, J.-Y., et al. Highly stretchable and tough hydrogels. *Nature* 489, 133-136 (2012).
17. Algi, M. P. & Okay, O. Highly stretchable self-healing poly (N, N-dimethylacrylamide) hydrogels. *European Polymer Journal* 59, 113-121 (2014).
18. Fitzgerald, M. M., Bootsma, K., Berberich, J. A. & Sparks, J. L. Tunable stress relaxation behavior of an alginate-polyacrylamide hydrogel: comparison with muscle tissue. *Biomacromolecules* 16, 1497-1505 (2015).
19. Bauer, A., et al. Hydrogel substrate stress-relaxation regulates the spreading and proliferation of mouse myoblasts. *Acta biomaterialia* 62, 82 (2017).
20. Chaudhuri, O., et al. Hydrogels with tunable stress relaxation regulate stem cell fate and activity. *Nature materials* 15, 326-334 (2016).
21. Schmoller, K. M. & Bausch, A. R. Similar nonlinear mechanical responses in hard and soft materials. *Nature materials* 12, 278-281 (2013).
22. Yue, Y., et al. Mechano-actuated ultrafast full-colour switching in layered photonic hydrogels. *Nature communications* 5, 4659 (2014).
23. Weng, L., Chen, X. & Chen, W. Rheological characterization of in situ crosslinkable hydrogels formulated from oxidized dextran and N-carboxyethyl chitosan. *Biomacromolecules* 8, 1109-1115 (2007).
24. Yan, C. & Pochan, D. J. Rheological properties of peptide-based hydrogels for biomedical and other applications. *Chemical Society Reviews* 39, 3528-3540 (2010).
25. Gasik, M., Gantar, A. & Novak, S. Viscoelastic behaviour of hydrogel-based composites for tissue engineering under mechanical load. *Biomedical Materials* 12, 025004 (2017).

26. Zhu, L., Qiu, J. & Sakai, E. A high modulus hydrogel obtained from hydrogen bond reconstruction and its application in vibration damper. *RSC Advances* 7, 43755-43763 (2017).
27. Meyvis, T. K., et al. A comparison between the use of dynamic mechanical analysis and oscillatory shear rheometry for the characterisation of hydrogels. *International journal of pharmaceutics* 244, 163-168 (2002).

Each publication, patent, and patent publication cited in this disclosure is incorporated in reference herein in its entirety. The present invention is not intended to be limited to the foregoing examples, but encompasses all such modifications and variations as come within the scope of the appended claims.

We claim:

1. A stretchable hydrogel comprising (i) polymerized and crosslinked N,N'-dimethylacrylamide (DMA) and (ii) non-crosslinked polyethylene oxide (PEO) forming a semi-interpenetrating polymer network (IPN), wherein the stretchable hydrogel is able to increase its length 100-260 times its original length when stretched.

2. The stretchable hydrogel of claim 1, wherein the hydrogel consists essentially of (i) polymerized and crosslinked DMA and (ii) non-crosslinked PEO.

3. The stretchable hydrogel of claim 1, wherein the hydrogel has about 100% increase in stress relaxation after more than 20 hours from 0.1N to 0.2N.

4. The stretchable hydrogel of claim 1, wherein the hydrogel is able to return to pre-stretched size after being stretched 100-200 times its length.

5. A composition comprising the stretchable hydrogel of claim 1.

6. The composition of claim 5, wherein the composition is a composition for wound care.

7. The composition of claim 6, wherein the stretchable hydrogel is formed into a contour forming wound covering.

8. The composition of claim 5, wherein the composition further comprises an embedded electronic device.

9. The composition of claim 8, wherein the embedded electronic device is a heart rate monitor, a heart rate electrode, a heart rhythm monitor, or a heart rhythm electrode.

10. A method of making a stretchable hydrogel able to increase its length by 100-260 times its initial length, the method comprising the step of:
    (a) polymerizing N,N'-dimethylacrylamide (DMA) in the presence of polyethylene oxide (PEO), thereby forming a semi-interpenetrating polymer network (IPN) to form a stretchable hydrogel comprising (i) polymerized and crosslinked DMA and (ii) non-crosslinked PEO.

11. The method of claim 10, wherein step (a) is performed at 50° C. with ammonium persulfate as an initiator and N,N-methylenebisacrylamide as a crosslinking agent to polymerize the DMA and PEO.

12. The method of claim 11, wherein the DMA and PEO are incubated for at least one hour.

13. The method of claim 11, further comprising submersing the stretchable hydrogel in water for at least one hour after polymerization.

14. A drug delivery system comprising the stretchable hydrogel of claim 1 and a drug.

15. The composition of claim 8, wherein the electronic device comprises a sensor, wherein the sensor monitors one or more conditions within the subject.

16. The compositions of claim 15, wherein the one or more condition is selected from the group consisting of heart rate, heart rhythm, and temperature.

17. The composition of claim 9, wherein the electronic device comprises an electrode that provides reliable low impedance electrical contact with the skin for physiological measurements.

18. The composition of claim 17, wherein the composition comprises multiple electrodes that provide an electrocardiogram.

19. A method for providing an electrocardiogram, the method comprising contacting the composition of claim 9 with a subject to provide an electrocardiogram.

* * * * *